United States Patent [19]
Westby et al.

[11] Patent Number: 5,531,670
[45] Date of Patent: Jul. 2, 1996

[54] HEAT CONSERVING BANDAGE

[75] Inventors: Reidar Westby, Littlehampton; David W. Talbot, Newmarket, both of United Kingdom

[73] Assignee: Anette Dobloug, Sande i Vestfold, Norway

[21] Appl. No.: 256,529

[22] PCT Filed: Jan. 17, 1992

[86] PCT No.: PCT/NO92/00009

§ 371 Date: Sep. 19, 1994

§ 102(e) Date: Sep. 19, 1994

[87] PCT Pub. No.: WO93/13735

PCT Pub. Date: Jul. 22, 1993

[51] Int. Cl.⁶ .................................................. A61F 13/00
[52] U.S. Cl. ........................... 602/41; 602/58; 604/304
[58] Field of Search ..................... 128/379, 399, 128/402; 602/42, 43–59, 6, 8, 75; 604/304, 308

[56] References Cited

U.S. PATENT DOCUMENTS

| | | | |
|---|---|---|---|
| 4,470,417 | 9/1984 | Gruber | 128/402 |
| 4,898,592 | 2/1990 | Latzko et al. | 604/307 |
| 4,899,738 | 2/1990 | Parker | 602/8 |
| 4,994,049 | 2/1991 | Latzko et al. | 604/307 |
| 5,003,970 | 4/1991 | Parker et al. | 602/50 |
| 5,405,643 | 4/1995 | Scholz | 602/8 |
| 5,423,735 | 6/1995 | Callinan et al. | 602/6 |
| 5,474,522 | 12/1995 | Scholz et al. | 602/8 |

*Primary Examiner*—C. Fred Rosenbaum
*Assistant Examiner*—Perry E. Van Over
*Attorney, Agent, or Firm*—Rodman & Rodman

[57] ABSTRACT

A heat conserving bandage to cover human or animal tissue, comprising heat reflecting means (1) adjacent said tissue for reflecting heat from said tissue back to said tissue, insulation material means (2) covering said heat reflecting means (1), and textile means (3) covering said insulation material means (2). The heat reflecting means (1) includes a sandwiched structure of a first foil (1a) of plastics material adjacent said tissue, a second foil (1b) and bonded thereto. Further textile means (3') can be inserted between said heat reflecting means (1) and said human or animal tissue. Suitably, the textile means and the heat reflecting means are bonded together by sewing or by means of adhesive to create a pocket for receiving said insulation material means.

11 Claims, 8 Drawing Sheets

HEAT CONSERVING BANDAGE

The present invention relates to a heat-conserving bandage to cover human or animal tissue.

The present bandage finds particular application for treating muscular damages, inflammation of joints, tendons and connective tissues and other related defects, and is in particular related to the conservation of natural heat from the body.

The bandage is intended to conserve local heat by reflection and with a minimum heat absorption by the bandage. The bandage avoids application of chemical or natural local heat irritants which are normally required to stimulate local heat production at the relevant area of the body to be treated. The bandage includes a combination of known materials, combined and assembled in a new manner and applied in an area of usages for which no such bandages have yet been available or known. Still, the present bandage satisfies long felt needs in its field of application.

The heat-conserving bandage to cover human or animal tissue comprises, according to the invention, heat reflecting means adjacent said tissue for reflecting heat from said tissue back to said tissue, insulation material means covering said heat reflecting means, and textile means covering said insulation material means.

Said heat reflecting means includes a sandwich structure of a first foil of plastics material adjacent said tissue, a second foil of aluminium covering said first foil and bonded thereto, and a glass fibre weave covering said second foil and bonded thereto.

The first foil of plastics material is preferably made of polyester.

The thickness of said heat reflecting means is preferably in the range of 0.3–0.8 millimeters, and more preferably of a thickness equal to 0.65 millimeters.

The said insulation material means has a closed cell structure. Suitably, the insulation material means is made from neoprene rubber or polyethylene. The insulation material means has preferably a thickness in the range between 2 and 16 millimeters.

Said textile means is suitably a cotton structured textile having a hydrophilic coat.

Velcro means are suitably attached to said textile means for locking the bandage about a portion of the human or animal body.

If preferred, a further textile means can be inserted between said tissue and said heat reflecting means.

Also, said heat reflecting means and said textile means are suitably sewed or bonded together along corresponding edges thereof. If present, the further textile means is also sewed or bonded to said heat reflecting means. Thus, the insulation material means is received in a pocket between the heating reflecting means and the rearmost textile means.

These and other embodiments of the present invention will appear from the attached patent claims and the description below with reference to the attached drawing figures showing non-limitative examples of the present invention.

FIG. 1a illustrates a cross section of the bandage according to the present invention.

FIG. 1b illustrates an enlarged part of heat reflecting means in FIG. 1a.

Figures 1A, 1B:
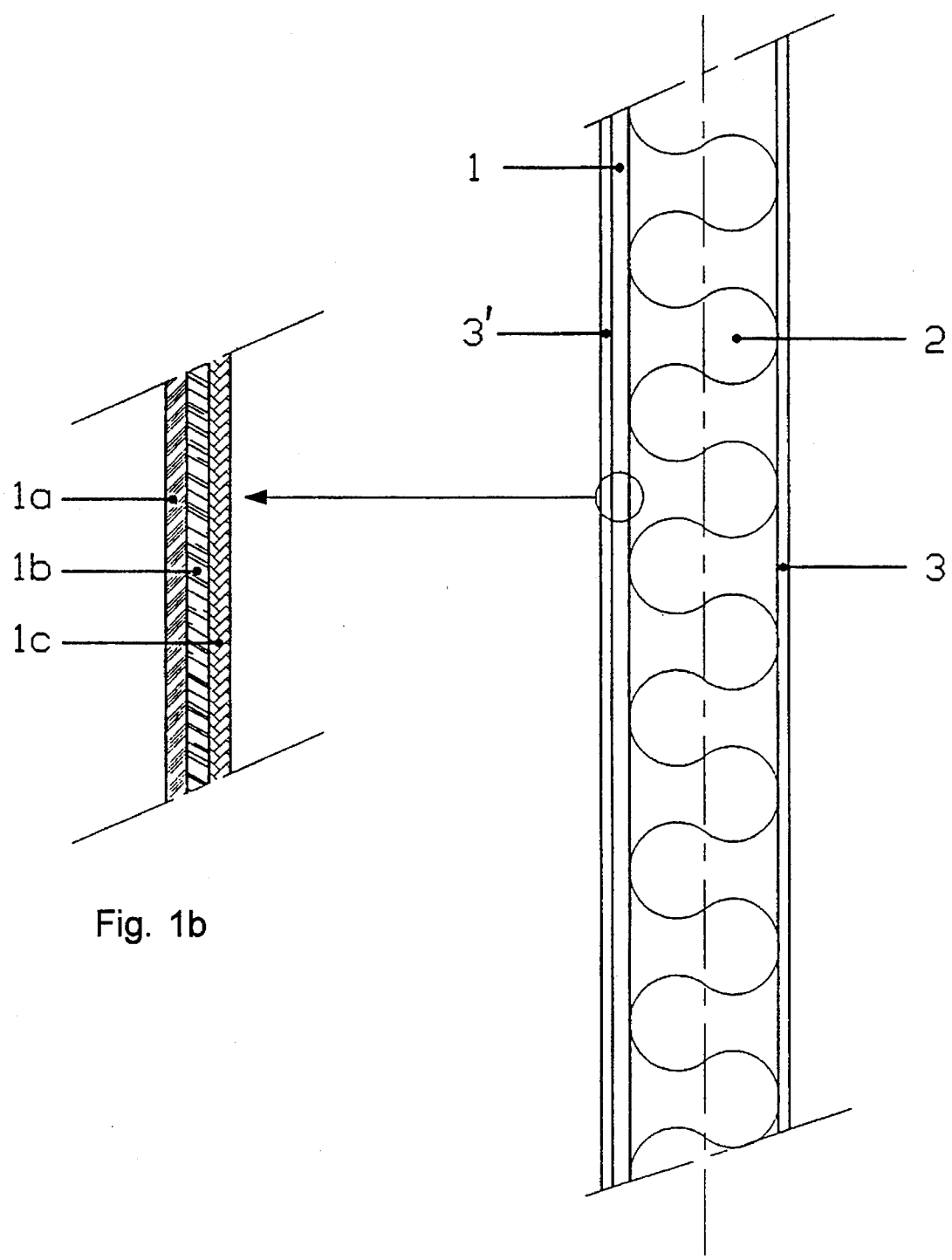

In the drawings, the heat reflecting means is denoted by reference numeral 1 and is made up from a glass fibre weave 1c bonded to an aluminium foil 1b, which is covered by a foil 1a of plastics material, suitably a transparent polyester. The overall thickness of the heat reflecting means is suitably 0.3–0.8 millimeter, and most preferably 0.65 millimeter.

The insulation material 2 is of a closed cell type and suitably made from neoprene rubber of polyethylene rubber. The thickness of the insulation material 2 is suitably between 2 and 16 millimeters.

The bandage has suitably on its rearmost part a cotton structured textile which covers the insulation material.

Suitably, the textile has hydrophillic coat. The thickness of the textile is suitably 0.1–0.65 millimeters. In certain instances, it is preferred to have further textile between the heat reflecting material and the tissue to be covered. That further textile material is labelled 3' and could be of the same type as the textile 3 just described.

Figure 2:
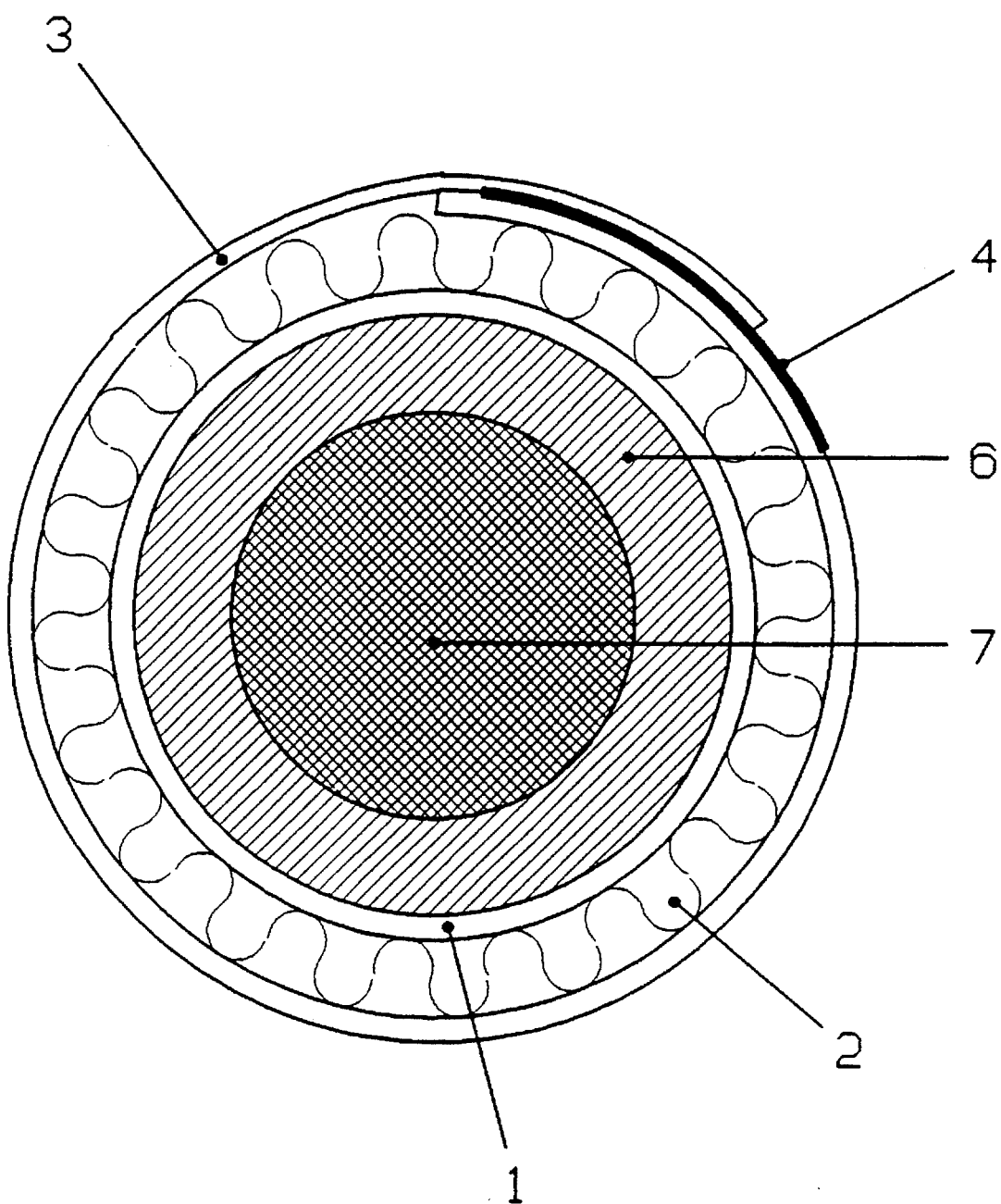
FIG. 2 illustrates the bandage wrapped about a bone structure covered by tissue.
Figure 3:
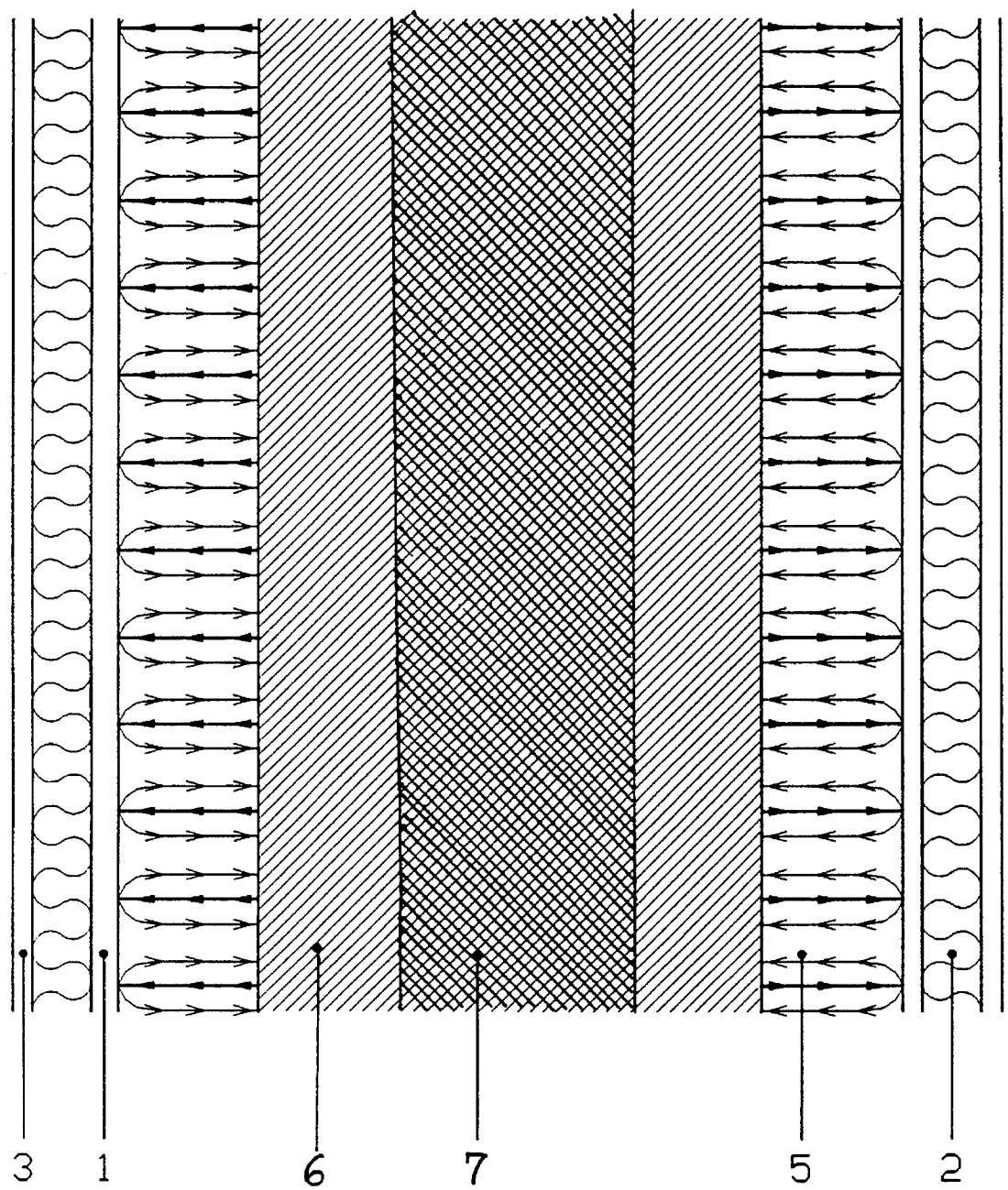
FIG. 3 illustrates heat transport and reflection related to the present bandage.

In FIGS. 2 and 3, the bandage is shown without such further textile 3', although it will be appreciated that such further textile 3' could be inserted between the tissue 6 of the human or animal body and the said heat reflecting means 1. In FIG. 2, it is illustrated how the bandage is wrapped around a tissue 6 with a central bone 7. Such body structure is e.g. found in a leg or arm. In order to facilitate easy locking of the bandage, Velcro means 4 are attached to the textile material 3 and provide easily adjustable locking means for said bandage.

In FIG. 3 the reference numeral 5 illustrates schematically the heat transport and reflection provided by the heat reflection material 1.

Figure 4:
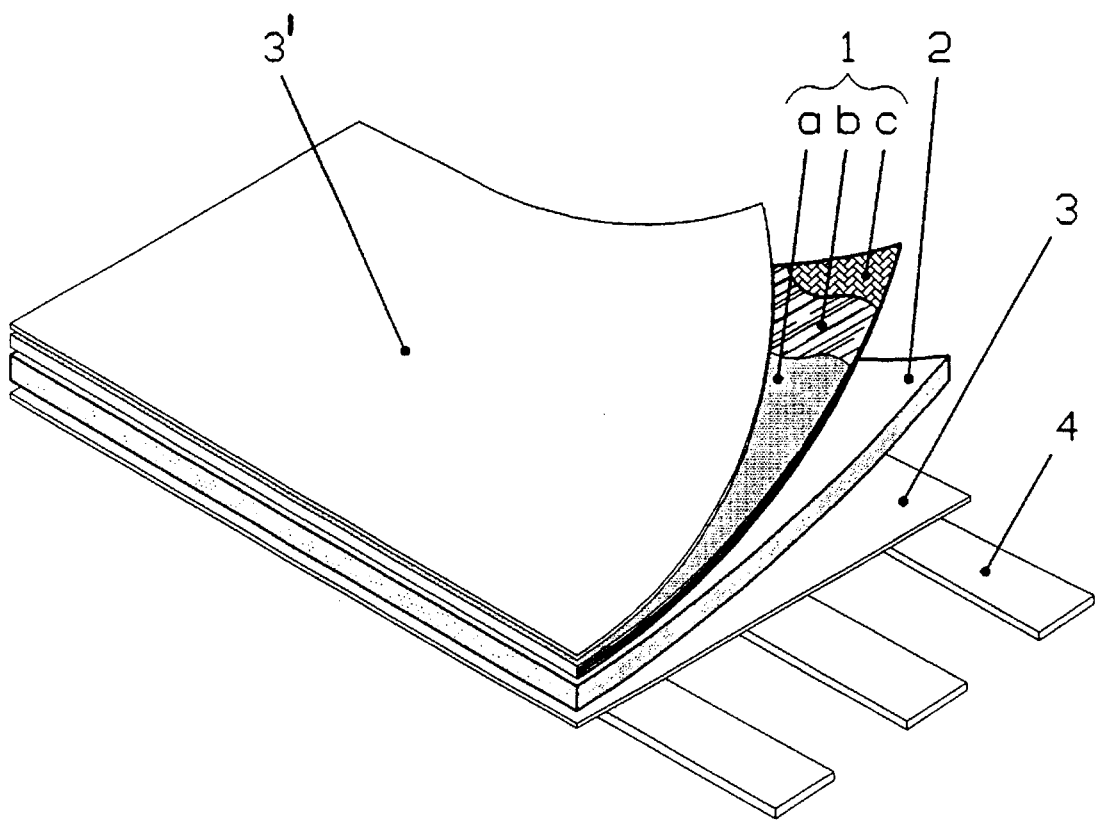
FIG. 4 illustrates structural build-up of the bandages of FIGS. 1 and 3.

In FIG. 4, it is noted that the bandage layers 1a, b and c are bonded together in a sandwich structure. It is preferable to sew the heat reflecting material 1 and the textile 3 (and possibly also the textile 3') together along at least three corresponding edges thereof, or join these bandage elements by other means of bonding, e.g. by adhesive means.

Figure 5:
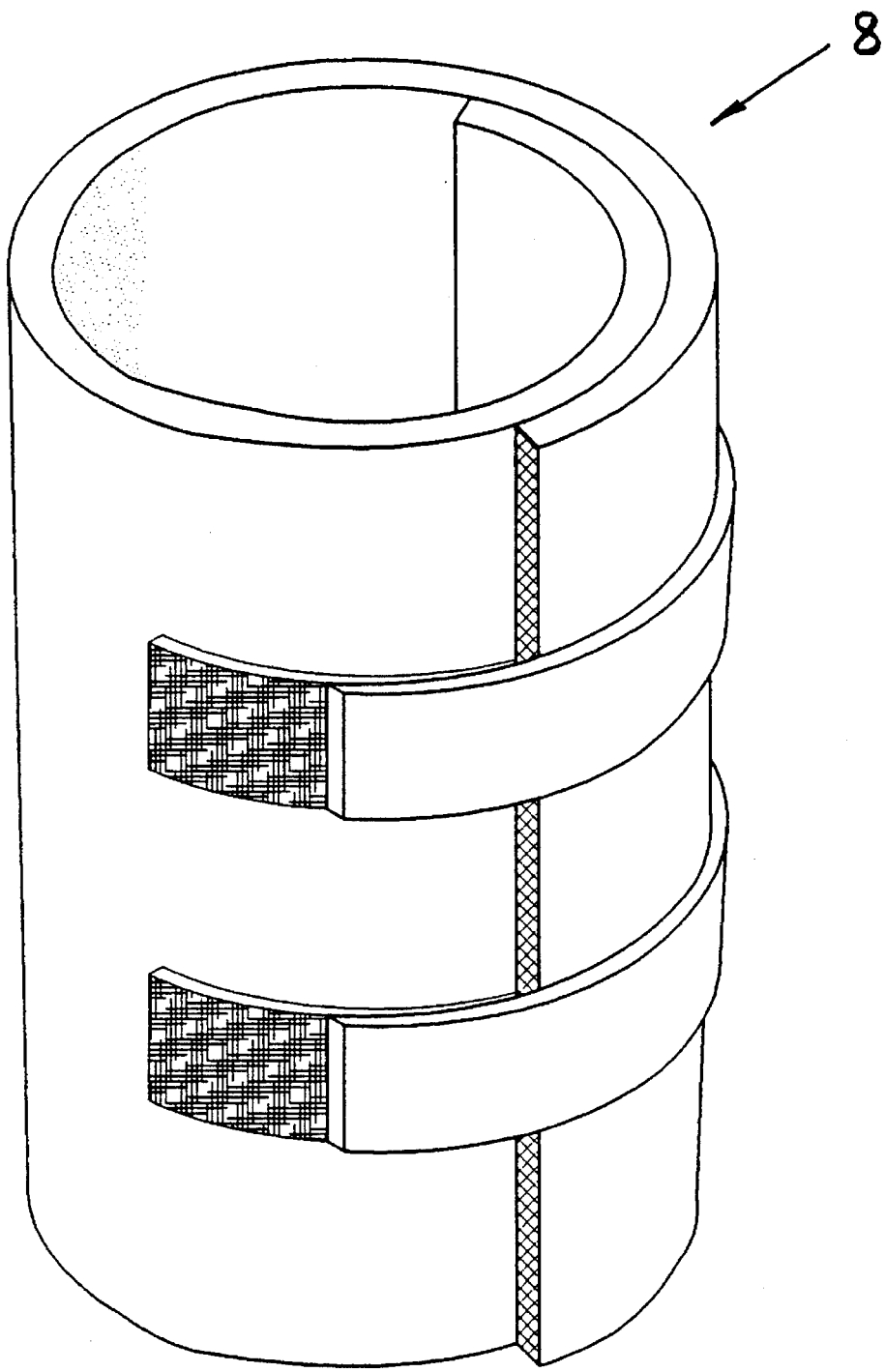
FIG. 5 illustrates the bandages shown in FIG. 2 in a perspective view without the bone and tissue shown.

FIG. 5 illustrates the bandages in the form it has when wrapped around e.g. an arm or a leg. The bandage is for sake of simplicity labelled 8 in FIG. 5.

Figure 6:
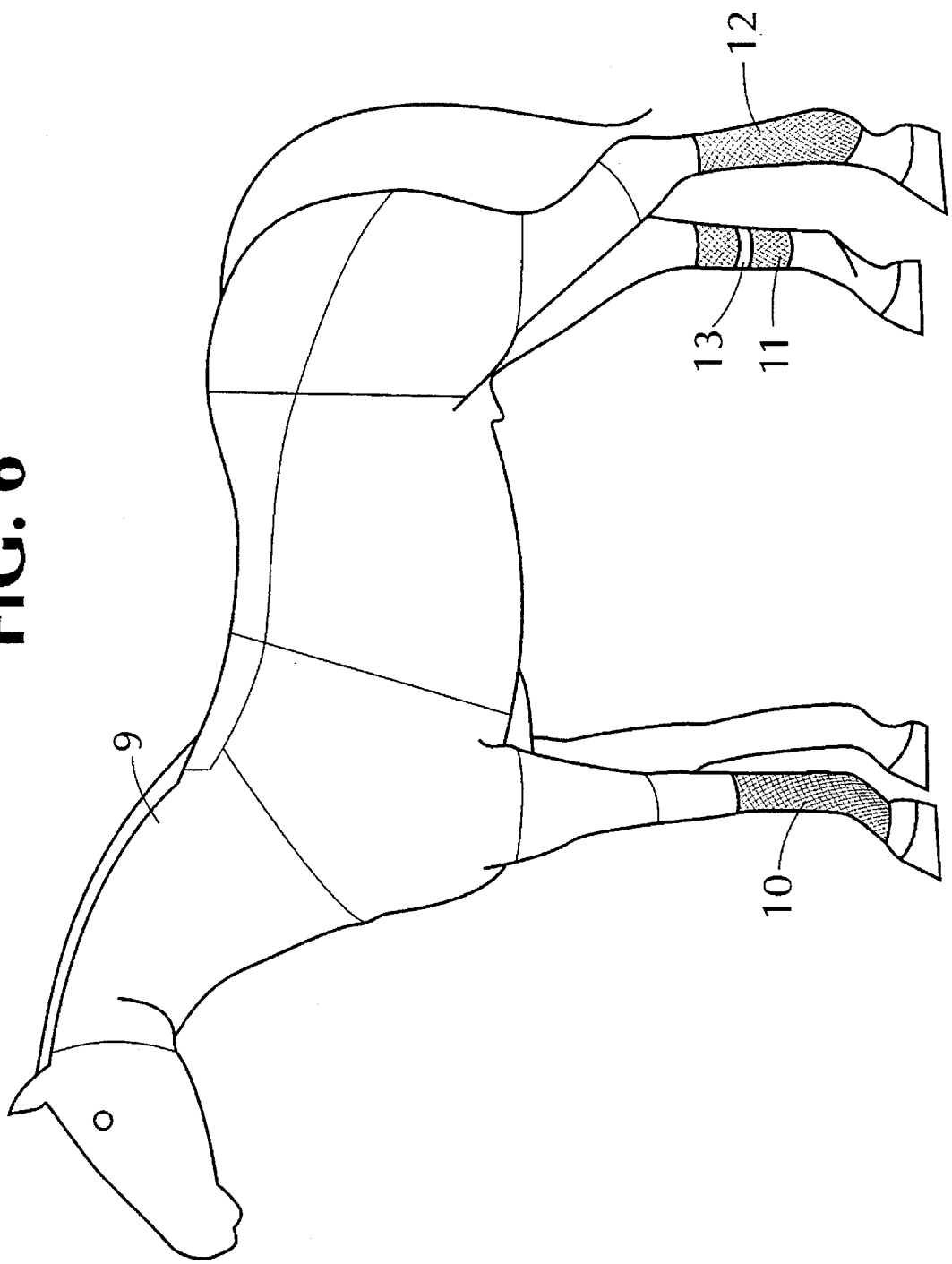
FIG. 6 illustrates the use of bandage on a horse.

In FIG. 6, it is illustrated a horse 9 having bandages 10, 11 and 12, said bandages being constructed according to the principles of the present invention. Suitably, the bandage 11 may be provided with light reflection means 13, although such means have no bearing on the present inventive concept.

Figure 7:
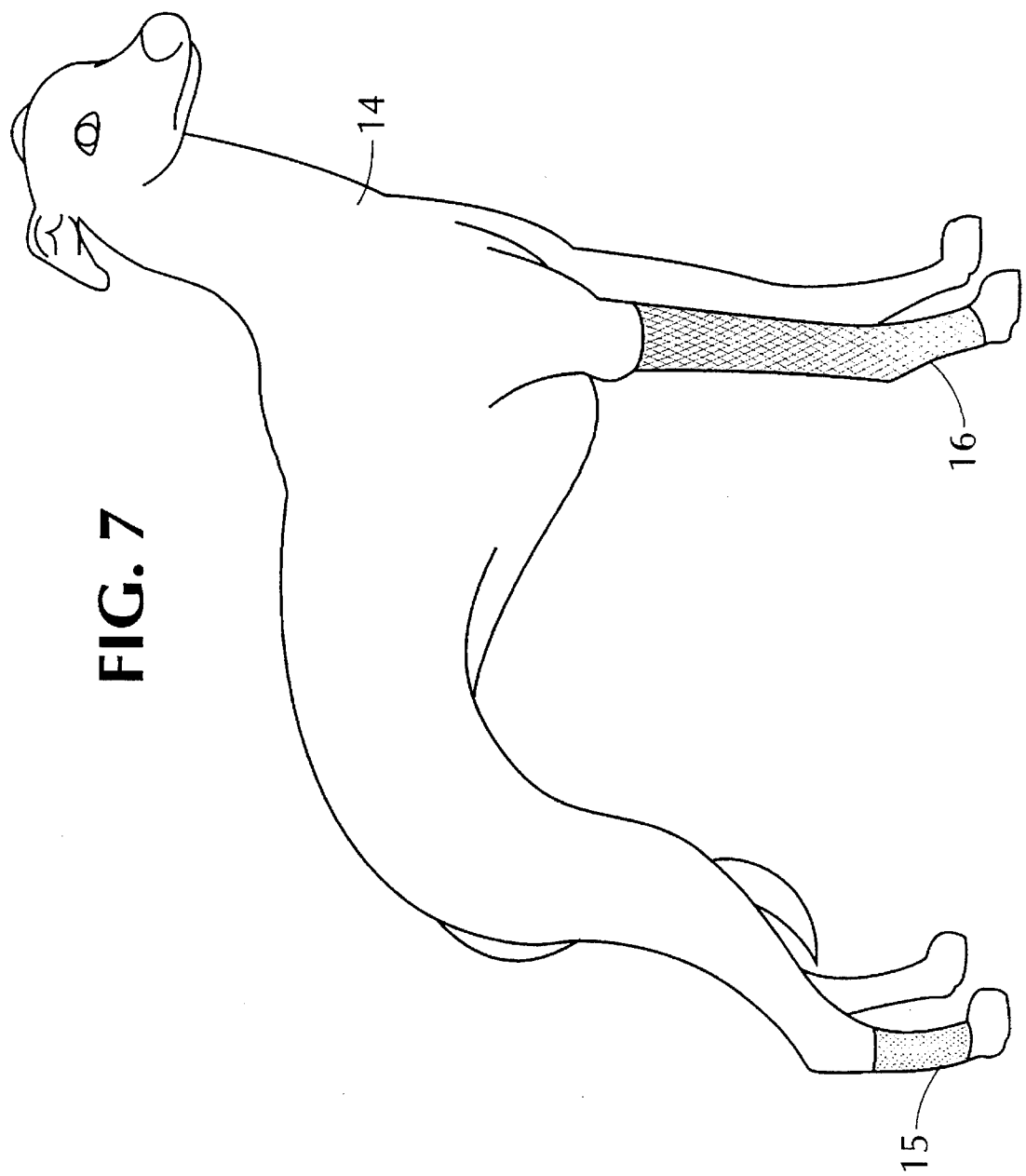
FIG. 7 illustrates the use of the inventive bandage on a dog.

FIG. 7 illustrates a dog 14 having bandages 15 and 16 on rear and front legs, respectively, said bandages being made according to the principles of the present invention.

Figure 8:
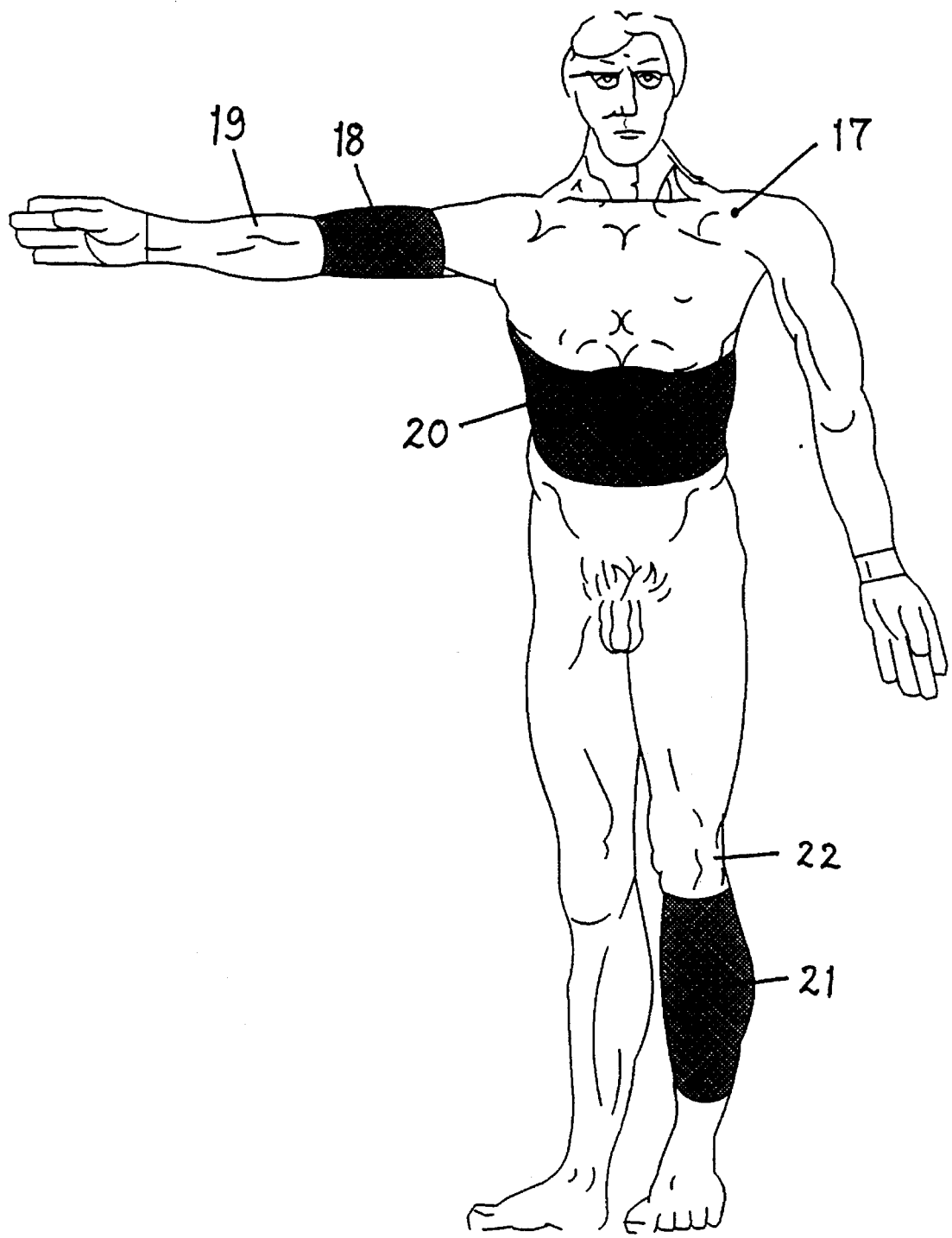
FIG. 8 illustrates the use of the bandage on a human being.

FIG. 8 illustrates a human being 17 having a bandage 18 on an arm 19, a further bandage 20 about the abdomen or lower chest of said human being, and a bandage 21 about a leg 22 of said human being.

It will be readily understood from the drawing FIGS. 6–8 that the positioning of the bandages are examples only and that different locations of bandages, shaping thereof and the number of bandages on the body can be varied without restricting the inventive concept and scope of the present invention.

Thus, the bandage can be used on any muscle groups or tissue that require a heat treatment.

The present invention is now to be further described with reference to some tests which have been made using the present bandages for treating physical problems related to a horse.

The bandage type used for the various tests was of the horse stable wrap. The position of the wrap was approximately 2.5 cm below knee/hock to 5 cm below fetlock joint. The fitting method wrap around the leg was based on a velcro locking system.

The objective of the bandage was to conserve heat in a specific area, and to bring up the temperature under the bandage without the assistance of a chemical or natural irritant.

The theory of heat applied to the leg of a horse, in order to assist circulation and reduce certain swellings, is not a new supposition. However, systems employed to date, do in most cases have certain drawbacks with negative side effects, and illegality of certain substances prior to some competitions.

Typical areas of use are: sprains, concussion related problems, impact traumas and poor lower leg circulation. The initial reaction of the leg of the horses after one of these problems is to swell to an indeterminable degree, so that the wrap must be loosely fitted and have the ability to compress, if the leg swells more than expected.

EXAMPLES

1.

Case: Four Years Old Warm Blood Trotting Horse

Problem: Soft fluid swellings above one hind fetlock joint, commonly called windgalls. Though not large swellings, they were unsightly. The wrap was fitted for a period of one hour, and removed to check the temperature. The leg had sweated directly over the swellings only, and the swellings had gone, the wrap was placed back on the leg for one day, and not replaced. The swellings did not return during the period of examination which was for two weeks.

2.

Case: Three Year Old Racehorse

Problem: Trauma to the near fore fetlock joint, with some degree of pain, and a swelling. No opening of the skin was present. The bandage was fitted for a period of twelve hours and removed. No swelling was present. Perspiration had occurred directly over the joint only. The bandage was replaced for twenty-four hours and removed. No pain or swelling was present. The bandage was left off, and pain and swelling did not return.

3.

Case: Three Year Old Racehorse

Problem: Due to a severe injury to the hock, the horse was confined to the stable for several months. Due to inactivity the lower part of the leg, below the injury had swollen. Two bandages were fitted, one to the damaged leg and one to the good leg for a period of twenty-four hours and then removed. The swollen leg had sweated profusely, and the swelling had been reduced significantly. The good leg, when the bandage was removed, was warm only, and just on the point of sweat. The bandages were identical.

4.

Case: Three Year Old Racehorse

Problem: Horse had kicked the stable wall with its hind leg. The injury was only a few hours old. A swelling was present with no breaks in the skin. The bandage was used for eight hours and removed. Sweating had occurred directly over the swelling, and the swelling had gone. The bandage was not replaced and the swelling did not reoccur.

5.

Case: Five Year Old Race Horse

Problem: Severe hard swelling over and around the fetlock joint, extending up the leg 17 cm. The horse had received all possible types of attention, over a period of 18 months, but with limited results. This treatment included a surgical draining. Due to the effect of this on his back leg, it was not possible to train this horse for racing. The bandage was fitted and left in place for 24 hours. When the bandage was removed, it was noted small circular rings of sweat of 2.5 cm in diameter on either side of the main lump. The bandage was replaced. Over a period of 3 days the sweating effect increased until it covered the entire mass, but only the mass and not the rest of the area covered by the bandage. After one week, a reduction in the overall mass could be observed by as much as one centimeter daily. After 6 weeks of treatment which was almost 24 hours per day, no blistering or any signs of irritation were present. After 8 weeks of treatment, it was noted that the mass had been reduced to 5 cm in length, and still showed signs of reducing. The shoes were changed and it was noted that on the bandage leg, the hoof growth had increased 3 times more than the unbandaged legs. There were still no negative side effects on the skin. Hair growth had also increased under the bandage. The mass had been reduced to such an extent that the horse was capable to resume racing training.

Cases 1–5 In General

The bandage has been extensively tested and to date no negative side effects have been shown. The bandage, if used on all four legs of the horse, has clearly illustrated that only the leg or legs that have a problem will sweat, and then only over the problem area. No real table does yet exist for time of healing in these cases, but the use of the bandage clearly demonstrates in similar traumas, attended with conventional remedies, that the time of recovery is far more effective with the use of the inventive bandage.

Further Examples Related To Human Beings

After the positive results for the bandage used on animals, in particular horses, it was decided to investigate similar types of injuries on human beings and to find out whether the bandage had same positive results in such cases.

The following traumas were elected for testing:

Sprained ligaments surrounding the knee, swollen calf muscle following a varicose vein removal, a whip lash injury to the neck, the lower part of the arm of a typist which had been a painful problem for several years, an arm of a stroke victim whose arm was always cold and with little movement of his fingers.

With the case of the sprained ligament, after the bandage was fitted the knee sweated for 3 days, and the pain was reported to be virtually non-existent, and the swelling had gone. The varicose problem reported significant reduction in size of the swelling. The whip lash injury reported an immediate reduction of pain. The stroke victim reported that the arm was warm and feeling had returned to his hand and fingers. The typist reported after one day that for the first time in several years, she had not felt the need for pain killing tablets.

Further testing is continuing, but the positive results so far are in line with the findings of the animal results.

The invention claimed is:

1. A heat conserving bandage to cover human or animal tissue comprising, a layer of heat reflecting material adapted for placement adjacent said tissue for reflecting heat from said tissue, a layer of insulation material having a closed cell structure covering said heat reflecting material, a layer of textile material covering said insulation material such that said insulation material is disposed between said heat reflecting layer and said textile layer, and wherein said heat reflecting material includes a sandwich structure of a first foil of plastic material adapted for placement adjacent said tissue, a second foil of aluminum covering said first foil and bonded thereto and a glass fiber weave layer covering said second foil and bonded thereto, such that said aluminum foil layer is disposed between said plastic foil and said glass fiber weave layer.

2. A heat conserving bandage according to claim 1, wherein said first foil of plastics material is made of polyester.

3. A heat conserving bandage according to claim 1, wherein the thickness of said heat reflecting means is in the range of 0.3–0.8 millimeters.

4. A heat conserving bandage according to claim 3, wherein the thickness of said heat reflecting means is 0.65 millimeters.

5. A heat conserving bandage according to claim 4, wherein said insulation material means is made from neoprene rubber or polyethylene rubber.

6. A heat conserving bandage according to claim 1, wherein said insulation material means has a thickness in the range between 2 and 16 millimeters.

7. A heat conserving bandage according to claim 1, wherein said textile means covering the rear of said insulation material means is a cotton structured textile having a hydrophilic coat.

8. A heat conserving bandage according to claim 1, wherein a further textile means is located between said tissue and said heat reflecting means, said further textile means being a cotton structured textile having a hydrophilic coat.

9. A heat conserving bandage according to claim 1, wherein said heat reflecting means and said textile means are sewed or bonded together along corresponding edges thereof to create a pocket for receiving said insulation material means.

10. A heat conserving bandage according to claim 1, wherein said further textile means, said heat reflecting means and said textile means are sewed or bonded together along corresponding edges thereof to create a pocket for receiving said insulation material means.

11. A heat conserving bandage comprising a heat reflecting layer including a laminate of plastic foil, aluminum foil and a glass fiber weave layer arranged such that the aluminum foil is disposed between the plastic foil and the glass fiber weave layer, a layer of insulation material covering said heat reflecting layer, a layer of textile material covering said insulation material, such that said insulation material is disposed between said heat reflecting layer and said textile layer, and securement means provided on said textile layer to permit opposite end portions of said heat conserving bandage to be secured in overlapping relationship, such that said layer of heat reflecting material encircles said tissue.

\* \* \* \* \*